US012329526B2

(12) United States Patent
Huang et al.

(10) Patent No.: US 12,329,526 B2
(45) Date of Patent: Jun. 17, 2025

(54) INFORMATION PROCESSING DEVICE, STATE DETERMINATION SYSTEM, ENERGY CALCULATION SYSTEM, INFORMATION PROCESSING METHOD, AND STORAGE MEDIUM

(71) Applicant: NEC Corporation, Tokyo (JP)

(72) Inventors: Chenhui Huang, Tokyo (JP); Kazuki Ihara, Tokyo (JP); Noriyuki Tonouchi, Tokyo (JP); Kenichiro Fukushi, Tokyo (JP)

(73) Assignee: NEC CORPORATION, Tokyo (JP)

(*) Notice: Subject to any disclaimer, the term of this patent is extended or adjusted under 35 U.S.C. 154(b) by 800 days.

(21) Appl. No.: 17/617,368

(22) PCT Filed: Jun. 12, 2019

(86) PCT No.: PCT/JP2019/023357
§ 371 (c)(1),
(2) Date: Dec. 8, 2021

(87) PCT Pub. No.: WO2020/250354
PCT Pub. Date: Dec. 17, 2020

(65) Prior Publication Data
US 2022/0225918 A1 Jul. 21, 2022

(51) Int. Cl.
A61B 5/22 (2006.01)
A61B 5/00 (2006.01)
A61B 5/11 (2006.01)

(52) U.S. Cl.
CPC ............ A61B 5/221 (2013.01); A61B 5/1118 (2013.01); A61B 5/1123 (2013.01); A61B 5/6829 (2013.01)

(58) Field of Classification Search
CPC ..... A61B 5/221; A61B 5/1118; A61B 5/1123; A61B 5/6829
See application file for complete search history.

(56) References Cited

U.S. PATENT DOCUMENTS

| 8,122,773 | B2* | 2/2012 | Wyatt | ............. G01L 3/24 73/818 |
| 9,650,106 | B1* | 5/2017 | Singh | ............. B62M 1/36 |
| 10,416,186 | B2* | 9/2019 | Nichols | ............. G01P 3/00 |
| 2008/0200312 | A1 | 8/2008 | Tagliabue | |

(Continued)

FOREIGN PATENT DOCUMENTS

JP 2004-345400 A 12/2004
JP 2010125239 A 6/2010
(Continued)

OTHER PUBLICATIONS

International Search Report for PCT Application No. PCT/JP2019/023357, mailed on Jul. 30, 2019.
(Continued)

Primary Examiner — Elias Desta
(74) Attorney, Agent, or Firm — Sughrue Mion, PLLC

(57) ABSTRACT

Provided is an information processing device including an acquisition unit configured to acquire motion information of a foot of a user measured by a motion measurement device and a determination unit configured to determine whether or not the user is in a pedaling state in which the user pedals a bicycle based on an angle between a sole and a ground generated from the motion information.

20 Claims, 11 Drawing Sheets

(56) References Cited

U.S. PATENT DOCUMENTS

| | | |
|---|---|---|
| 2015/0127126 A1 | 5/2015 | Yamagata et al. |
| 2017/0296896 A1 | 10/2017 | Shen et al. |
| 2019/0038938 A1 | 2/2019 | Nagasaka et al. |
| 2019/0143894 A1 | 5/2019 | Ikeda et al. |
| 2019/0328304 A1 | 10/2019 | Uchida et al. |

FOREIGN PATENT DOCUMENTS

| | | |
|---|---|---|
| JP | 5202257 B2 | 6/2013 |
| JP | 5270580 B2 | 8/2013 |
| JP | 2015109946 A | 6/2015 |
| JP | 2017065632 A | 4/2017 |
| JP | 2018014031 A | 1/2018 |
| JP | 2018102579 A | 7/2018 |
| JP | 2019025229 A | 2/2019 |

OTHER PUBLICATIONS

Sebastian O.H. Madgwick et al,"Estimation of IMU and MARG orientation using a gradient descent algorithm", 2011 IEEE International Conference on Rehabilitation Robotics Rehab Week Zurich, ETH Zurich Science City, Switzerland, Jun. 29-Jul. 1, 2011, pp. 1-7.
Japanese Office Action for JP Application No. 2021-525485 mailed on May 26, 2022 with English Translation.

\* cited by examiner

INFORMATION PROCESSING DEVICE, STATE DETERMINATION SYSTEM, ENERGY CALCULATION SYSTEM, INFORMATION PROCESSING METHOD, AND STORAGE MEDIUM

This application is a National Stage Entry of PCT/JP2019/023357 filed on Jun. 12, 2019, the contents of all of which are incorporated herein by reference, in their entirety.

TECHNICAL FIELD

The present invention relates to an information processing device, a state determination system, an energy calculation system, an information processing method, and a storage medium.

BACKGROUND ART

Patent Literature 1 discloses a device for determining a pose using an acceleration sensor mounted on a human body. The device of the Patent Literature 1 determines whether the person is walking, running, lying, sitting, or standing based on the three axial acceleration acquired by the acceleration sensor.

CITATION LIST

Patent Literature

PTL 1: Japanese Patent Application Laid-open No. 2010-125239

Non Patent Literature

NPL 1: Sebastian O. H. Madgwick, Andrew J. L. Harrison, and Ravi Vaidyanathan, "Estimation of IMU and MARG orientation using a gradient descent algorithm", 2011 IEEE International Conference on Rehabilitation Robotics, pp. 179-185, 2011.

SUMMARY OF INVENTION

Technical Problem

The acceleration acquired by the acceleration sensor may include noise. When the pose determination method using acceleration as disclosed in Patent Literature 1 is applied to determination of a state of a user riding a bicycle, this noise may decrease determination accuracy.

The present invention intends to provide an information processing device, a state determination system, an energy calculation system, an information processing method, and a storage medium which can determine a state of a user with high accuracy.

Solution to Problem

According to one example aspect of the invention, provided is an information processing device including an acquisition unit configured to acquire motion information of a foot of a user measured by a motion measurement device and a determination unit configured to determine whether or not the user is in a pedaling state in which the user pedals a bicycle based on an angle between a sole and a ground generated from the motion information.

According to another example aspect of the invention, provided is an information processing method including acquiring motion information of a foot of a user measured by a motion measurement device and determining whether or not the user is in a pedaling state in which the user pedals a bicycle based on an angle between a sole and a ground generated from the motion information.

According to another example aspect of the invention, provided is a storage medium storing a program that causes a computer to perform acquiring motion information of a foot of a user measured by a motion measurement device and determining whether or not the user is in a pedaling state in which the user pedals a bicycle based on an angle between a sole and a ground generated from the motion information.

Advantageous Effects of Invention

According to the present invention, an information processing device, a state determination system, an energy calculation system, an information processing method, and a storage medium which can determine a state of a user with high accuracy can be provided.

Exemplary embodiments of the present invention are described below with reference to the drawings. Throughout the drawings, the same components or corresponding components are labeled with same references, and the description thereof may be omitted or simplified.

FIRST EXAMPLE EMBODIMENT

A state determination system according to the present example embodiment is described. The state determination system of the present example embodiment is a system for measuring and analyzing a state of a user including determination of the state of the user riding the bicycle. As a part of health management, there is a need to acquire a log related to exercise such as daily walking time, bicycle riding time, and the like. In order to acquire the log of the bicycle riding time of the user, a function of determining the state of the user riding the bicycle is required. Accordingly, the present example embodiment provides a state determination system capable of determining the state of the user riding the bicycle with high accuracy.

The state of the user riding the bicycle typically includes a pedaling state in which the user is pedaling the bicycle. In other words, the state determination system of the present example embodiment can determine whether or not the user is pedaling.

Even when the user is on the bicycle, a state in which the user is not pedaling is not included in the pedaling state. Such a state in which the user is not pedaling is called a non-pedaling state. In recent years, a bicycle which is commercially available has been provided with a freewheel mechanism so that the bicycle can be traveled by inertia without turning a pedal. In such riding of the bicycle, a state in which the bicycle is traveling with inertia without pedaling by the user is included in the non-pedaling state. Further, the non-pedaling state includes a state in which the user is not pedaling in the operation of a bicycle equipped with a motor, which is provided with both a pedal and a motor such as a moped and is capable of traveling with human power.

In this specification, the number of wheels included in the bicycle is not particularly limited, and the "bicycle" may include not only a two-wheel bicycle but also a three-wheel bicycle, a bicycle with an auxiliary wheel, and the like. Further, even a vehicle equipped with a motor such as an electrically assisted bicycle or a bicycle with a motor is included in "bicycle" as long as it is provided with a mechanism capable of being driven by a pedal with human power. Further, the "bicycle" includes a stationary bicycle such as a bicycle for indoor training having a pedal like a two-wheel bicycle.

Figure 1:
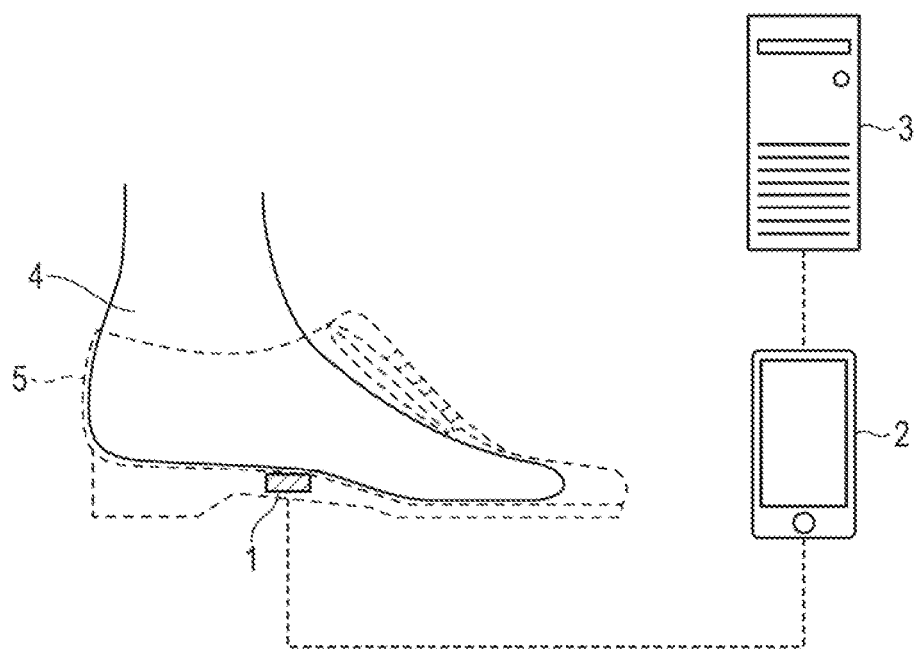
FIG. 1 is a schematic diagram illustrating a general configuration of a state determination system according to a first example embodiment.

FIG. 1 is a schematic diagram illustrating a general configuration of a state determination system according to the present example embodiment. The state determination system includes a state determination device 1, an information communication terminal 2, and a server 3 which can be connected to each other by wireless communication.

The state determination device 1 is provided to be close to the sole of a shoe 5 worn by a user 4, for example. The state determination device 1 is an electronic apparatus having a sensing function for measuring a motion of the foot of the user 4, an information processing function for analyzing the measured motion information, a communication function with the information communication terminal 2, and the like. It is desirable that the state determination device 1 be provided at a position corresponding to the arch of the foot such as just below the arch of the foot. In this case, the state determination device 1 can measure acceleration and angular velocity of the center of the foot of the user 4. Since the center of the foot is a position showing the feature of the motion of the foot well, it is suitable for extracting features indicating the state of the user.

Note that, the state determination device 1 may be provided in the insole of the shoe 5, may be provided in the outsole of the shoe 5, or may be embedded in the shoe 5. The state determination device 1 may be detachably attached to the shoe 5 or may be non-detachably fixed to the shoe 5. The state determination device 1 may be provided at a portion other than the shoe 5 as long as the state determination device 1 can measure the motion of the foot. For example, the state determination device 1 may be provided in a sock which the user 4 is wearing, provided in a decoration, directly attached to the foot of the user 4, or embedded in the foot of the user 4. Although FIG. 1 illustrates an example in which one state determination device 1 is provided on one foot of the user 4, one state determination device 1 may be provided on each of both feet of the user 4. In this case, the motion information of both feet can be acquired in parallel, and more information can be acquired.

In this specification, the "foot" means a body part below an ankle of the user 4. In addition, in this specification, the "user" means a person who is an object of a determination of the state using the state determination device 1. Whether or not the user corresponds to the "user" is unrelated to whether or not the user is a user of a device other than the state determination device 1 constituting the state determination system, whether or not the user receives a service provided by the state determination system, or the like.

The information communication terminal 2 is a terminal device carried by the user 4, such as a cellular phone, a smartphone, or a smart watch. Application software for analyzing a state is installed in advance in the information communication terminal 2, and processing based on the application software is performed. The information communication terminal 2 acquires data such as the state determination result acquired by the state determination device 1 from the state determination device 1 and performs information processing using the data. The result of the information processing may be notified to the user 4 or may be transmitted to the server 3. The information communication terminal 2 may have a function of providing software such as a control program of the state determination device 1 or a data analysis program to the state determination device 1.

The server 3 provides application software for analyzing states to the information communication terminal 2 and updates the application software. The server 3 may store data acquired from the information communication terminal 2 and perform information processing using the data.

Note that, the general configuration is an example, and for example, the state determination device 1 may be directly connected to the server 3. Further, the state determination device 1 and the information communication terminal 2 may be configured as an integrated device, and another device such as an edge server or a relay device may be further included in the state determination system.

Figure 2:
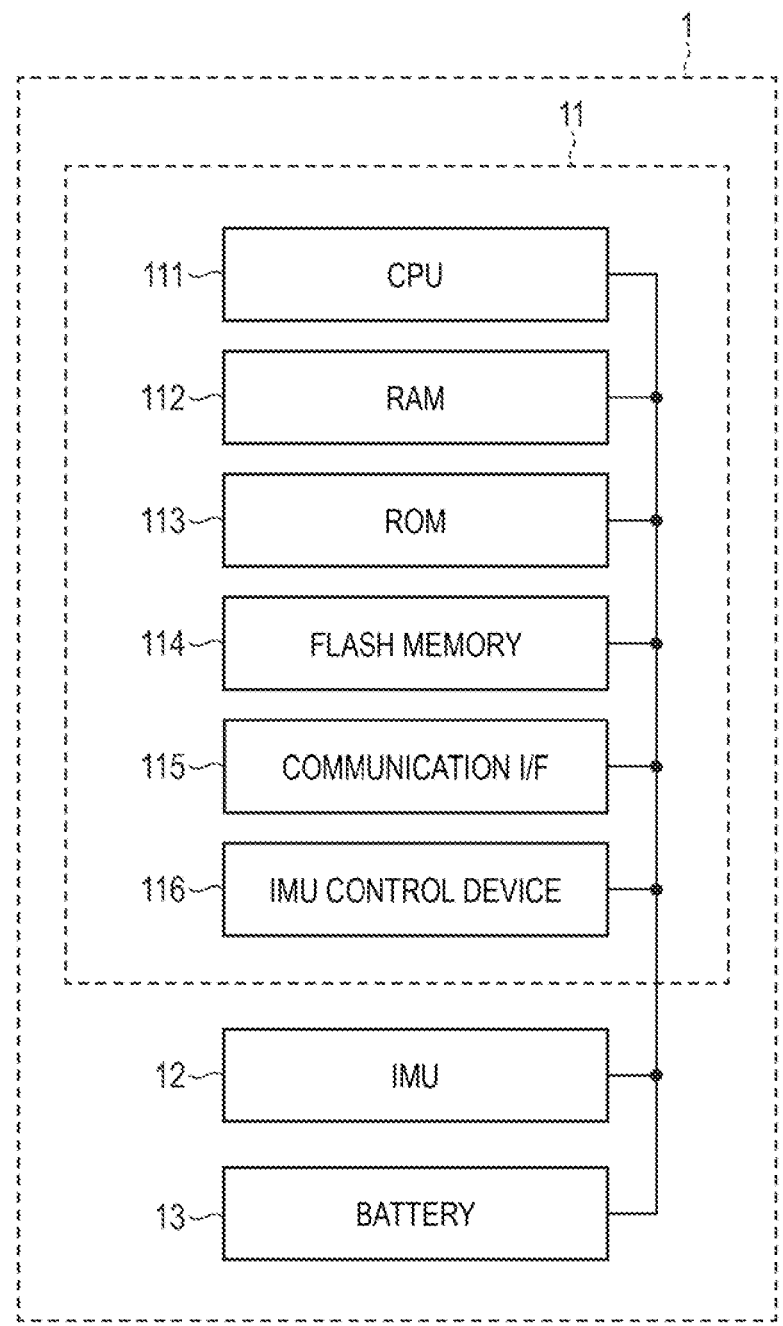
FIG. 2 is a block diagram illustrating a hardware configuration of a state determination device according to the first example embodiment.

FIG. 2 is a block diagram illustrating a hardware configuration example of the state determination device 1. The state determination device 1 includes an information processing device 11, an inertial measurement unit (IMU) 12, and a battery 13.

The information processing device 11 is, for example, a microcomputer or a microcontroller that performs a control and data processing of the entire state determination device 1. The information processing device 11 includes a central processing unit (CPU) 111, a random access memory (RAM) 112, a read only memory (ROM) 113, a flash memory 114, a communication interface (I/F) 115, and an IMU control device 116. Each unit in the information processing device 11, the IMU 12, and the battery 13 is connected each other via a bus, wiring, a driving device, or the like.

The CPU 111 is a processor that performs predetermined calculation in accordance with a program stored in the ROM 113, the flash memory 114, or the like, and also has a function of controlling each unit of the information processing device 11. The RAM 112 is composed of a volatile storage medium and provides a temporary memory area required for the operation of the CPU 111. The ROM 113 is composed of a non-volatile storage medium and stores necessary information such as a program used for the operation of the information processing device 11. The flash memory 114 is a storage device composed of a non-volatile storage medium and temporarily storing data, storing an operation program of the information processing device 11, or the like.

The communication I/F 115 is a communication interface based on standards such as Bluetooth (registered trademark) or Wi-Fi (registered trademark), and is a module for performing communication with the information communication terminal 2.

The IMU 12 is a motion measurement device including an angular velocity sensor that measures angular velocity in three axial directions and an acceleration sensor that measures acceleration in three directions. The angular velocity sensor may be any sensor as long as it can acquire the angular velocity as time series data, and any type of sensor such as a vibration type sensor or a capacitance type sensor may be used. The acceleration sensor may be any type of sensor as long as it can acquire acceleration as time series data, and any type of sensor such as a piezoelectric type sensor, a piezoresistance type sensor, or a capacitance type sensor may be used. In the present example embodiment, the interval between the data points of the acquired time series data may be constant or may not be constant.

The IMU control device 116 is a control device that controls the IMU 12 to measure angular velocity and acceleration and acquires angular velocity and acceleration acquired by the IMU 12. The acquired angular velocity and acceleration are stored in the flash memory 114 as digital data. Note that analog-to-digital (AD) conversion for converting an analog signal measured by the IMU 12 into digital data may be performed in the IMU 12 or may be performed by the IMU control device 116.

The battery 13 is, for example, a secondary battery, and supplies power necessary for the operations of the information processing device 11 and the IMU 12. Since the battery 13 is built in the state determination device 1, the state determination device can operate wirelessly without connecting to an external power source by wire.

Note that the hardware configuration illustrated in FIG. 2 is an example, and other devices may be added or some devices may not be provided. Further, some devices may be replaced by other devices having similar functions. For example, the information processing device 11 may further include an input device such as a button so that an operation by the user 4 can be accepted, and may further include an output device such as a display, a display lamp, and a speaker for providing information to the user 4. Thus, the hardware configuration illustrated in FIG. 2 can be changed appropriately.

Figure 3:
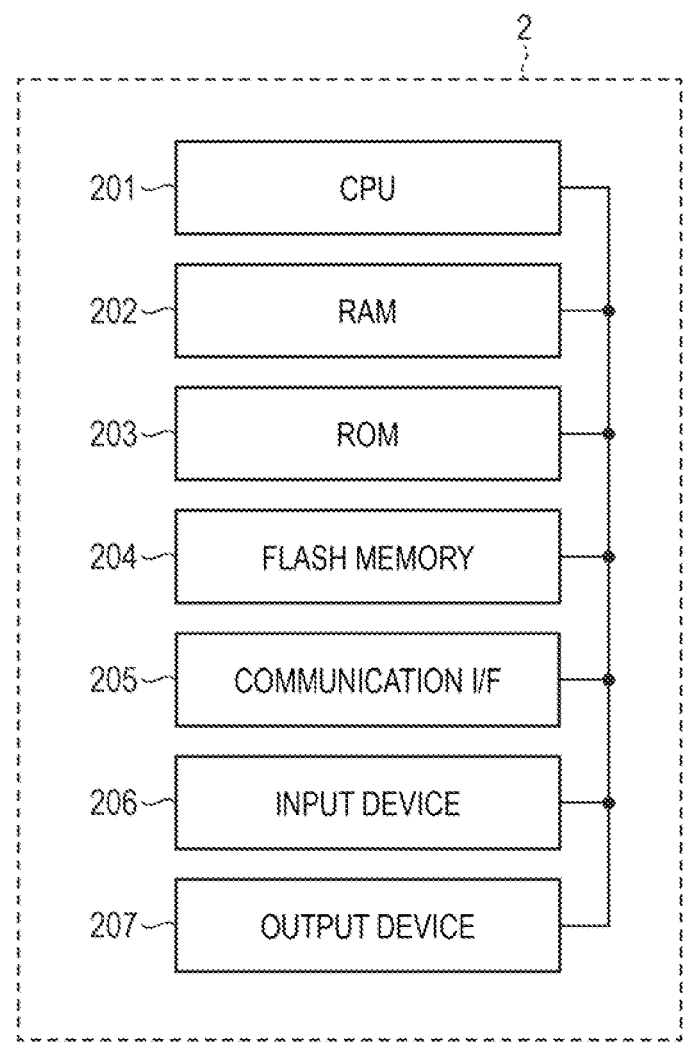
FIG. 3 is a block diagram illustrating a hardware configuration of an information communication terminal according to the first example embodiment.

FIG. 3 is a block diagram illustrating a hardware configuration example of the information communication terminal 2. The information communication terminal 2 includes a CPU 201, a RAM 202, a ROM 203, and a flash memory 204. The information communication terminal 2 also includes a communication I/F 205, an input device 206, and an output device 207. Each unit of the information communication terminal 2 is connected to each other via a bus, wiring, a driving device, or the like.

In FIG. 3, each unit constituting the information communication terminal 2 is illustrated as an integrated device, but a part of these functions may be provided by an external device. For example, the input device 206 and the output device 207 may be external devices different from those constituting the functions of the computer including the CPU 201 or the like.

The CPU 201 is a processor that performs predetermined calculation in accordance with a program stored in the ROM 203, the flash memory 204, or the like, and also has a function of controlling each unit of the information communication terminal 2. The RAM 202 is composed of a volatile storage medium and provides a temporary memory area required for the operation of the CPU 201. The ROM 203 is composed of a non-volatile storage medium and stores necessary information such as a program used for the operation of the information communication terminal 2. The flash memory 204 is a storage device composed of a non-volatile storage medium for storing data transmitted and received to and from the state determination device and for storing a program for operating the information communication terminal 2.

The communication I/F 205 is a communication interface based on standards such as Bluetooth (registered trademark), Wi-Fi (registered trademark), or 4G and is a module for performing communication with other devices.

The input device 206 is a user interface used by the user 4 to operate the information communication terminal 2. Examples of the input device 206 include a mouse, a trackball, a touch panel, a pen tablet, a button, or the like.

The output device 207 is, for example, a display device. The display device is a liquid crystal display, an organic light emitting diode (OLED) display, or the like, and is used for displaying information, displaying a graphical user interface (GUI) for operation input, or the like. The input device 206 and the output device 207 may be integrally formed as a touch panel.

Note that the hardware configuration illustrated in FIG. 3 is an example, and other devices may be added or some devices may not be provided. Further, some devices may be replaced by other devices having similar functions. Further, some functions of the present example embodiment may be provided by other devices via a network, or some functions of the present example embodiment may be realized by being distributed among a plurality of devices. For example, the flash memory 204 may be replaced by a hard disk drive (HDD) or a cloud storage. Thus, the hardware configuration illustrated in FIG. 3 can be changed appropriately.

The server 3 is a computer having substantially the same hardware configuration as that illustrated in FIG. 3. Since the hardware configuration of the server 3 is substantially the same as that of the information communication terminal 2 except that the server 3 may not be portable, a detailed description thereof is omitted.

Figure 4:
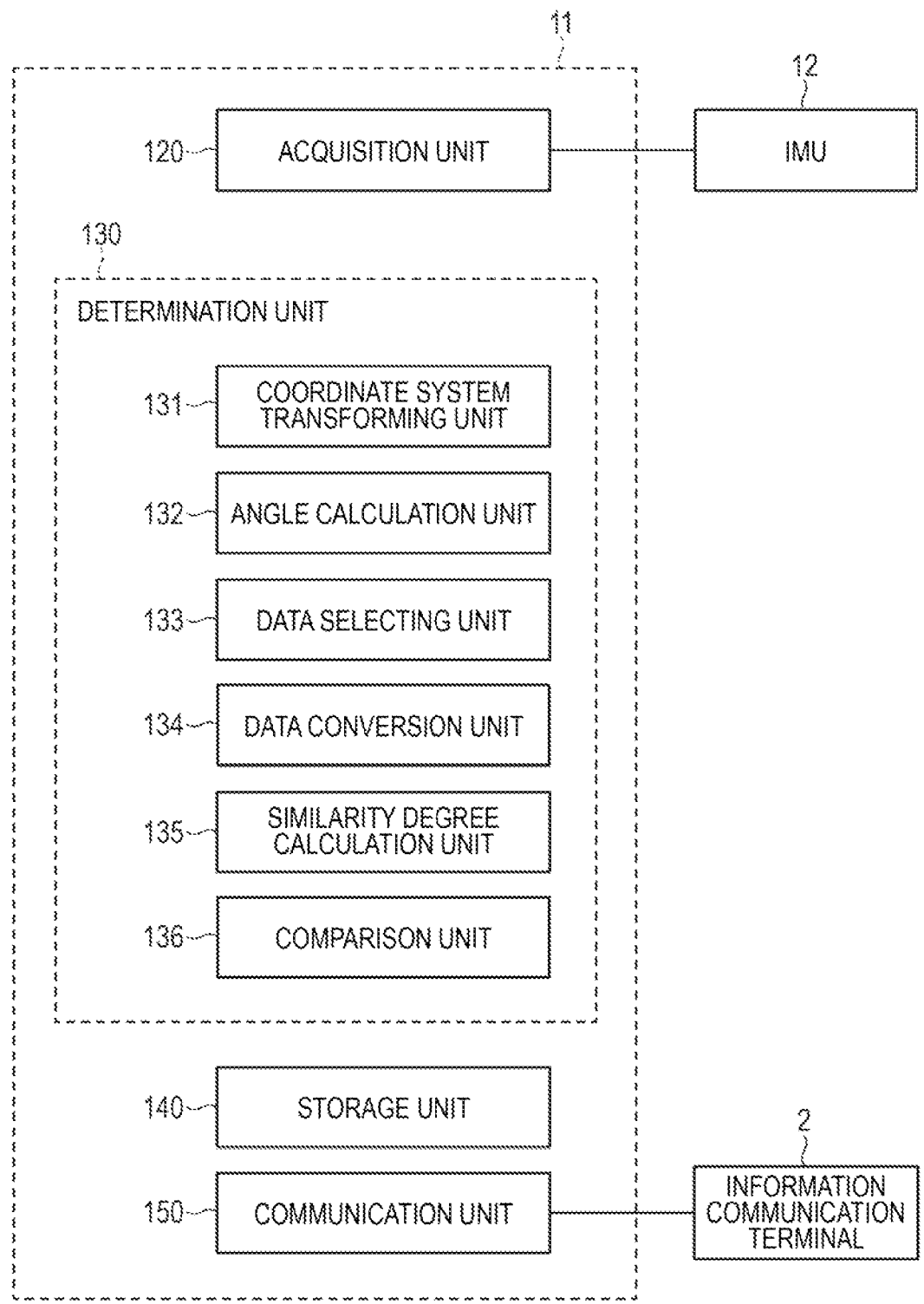
FIG. 4 is a functional block diagram of an information processing device according to the first example embodiment.

FIG. 4 is a functional block diagram of the information processing device 11 according to the present example embodiment. The information processing device 11 includes an acquisition unit 120, a determination unit 130, a storage unit 140, and a communication unit 150. The determination unit 130 includes a coordinate system transforming unit 131, an angle calculation unit 132, a data selecting unit 133, a data conversion unit 134, a similarity degree calculation unit 135, and a comparison unit 136.

The CPU 111 loads a program stored in the ROM 113, the flash memory 114, or the like into the RAM 112 and executes the program. Thus, the CPU 111 realizes the functions of the determination unit 130. Further, the CPU 111 realizes the function of the acquisition unit 120 by controlling the IMU control device 116 based on the program. The CPU 111 realizes the function of the storage unit 140 by controlling the flash memory 114 based on the program. Further, the CPU 111 realizes the function of the communication unit 150 by controlling the communication I/F 115 based on the program. Specific processing performed by each of these units is described later.

In the present example embodiment, each function of the functional blocks illustrated in FIG. 4 is provided in the state determination device 1, but some functions of the functional blocks illustrated in FIG. 4 may be provided in the information communication terminal 2 or the server 3. That is, the above-described functions may be realized by any of the state determination device 1, the information communication terminal 2, and the server 3, or may be realized by cooperation of the state determination device 1, the information communication terminal 2, and the server 3.

Figure 5:
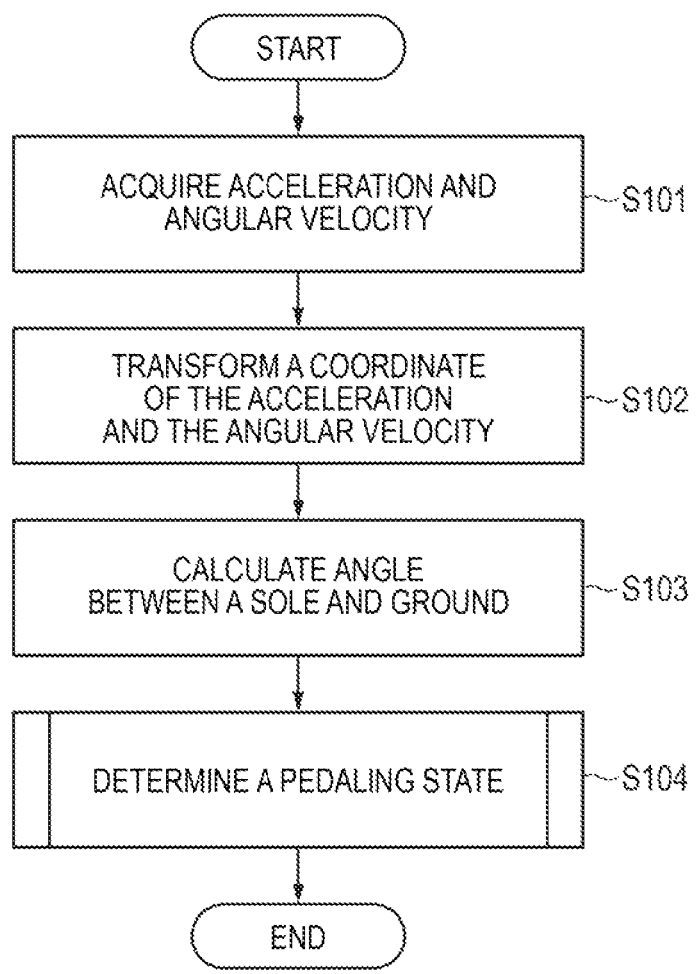
FIG. 5 is a flowchart illustrating an example of a state determination process performed by the state determination device according to the first example embodiment.

FIG. 5 is a flowchart illustrating an example of a state determination process performed by the state determination device 1 according to the present example embodiment. The process of FIG. 5 is performed at predetermined time intervals, for example. Alternatively, the process of FIG. 5 may be performed when the state determination device 1 detects that the user 4 has got on the bicycle based on a change in acceleration or the like.

In step S101, the acquisition unit 120 controls the angular velocity sensor and the acceleration sensor of the IMU 12 to acquire time series data of angular velocity in three axial directions and acceleration in three directions. Thus, the acquisition unit 120 can acquire time changes in angular velocity and acceleration based on the motion of the foot of the user 4. The acquired time series data of angular velocity and acceleration is converted into digital data and then stored in the storage unit 140. These angular velocity and acceleration are referred to more generally as motion information.

The three directions of acceleration acquired by the acquisition unit 120 may be, for example, the width direction (left/right direction), the longitudinal direction (front/back direction), and the vertical direction of the foot of the user 4 provided with the IMU 12. These directions are referred to as x-axis, y-axis, and z-axis, respectively. The three axial directions of the angular velocity acquired by the acquisition unit 120 may be, for example, an adduction and an abduction of the foot about the z-axis (yaw), a pronation and a supination of the foot about the y-axis (pitch), and a bending and a stretching of the foot about x-axis (roll).

Here, in order to sufficiently acquire the feature included in the pedaling, it is desirable that the time series data of the angular velocity in the three axial directions and the acceleration in the three directions include data in a period corresponding to at least two pedaling cycles (rotation time corresponding to two cycles of the pedal). This is because the pedaling is a substantially periodic circular motion, and therefore, if at least two cycles can be extracted, it can be estimated that the same motion is repeated before and after the two cycles.

In step S102, the coordinate system transforming unit 131 performs coordinate system transformation of angular velocity in three axial directions and acceleration in three directions. A coordinate system with respect to angular velocity and acceleration output by the IMU 12 is an inertial coordinate system. The coordinate system transforming unit 131 transforms the angular velocity and acceleration coordinate system into a coordinate system with respect to the foot of the user 4. Thus, the coordinate system of the angular velocity and the acceleration can be made suitable for calculating the angle between the sole and the ground. The transformation of the coordinate system is realized, for example, by multiplying the base vector of the inertial coordinate system by the direction cosine matrix E using the Euler angle and rotating the base vector.

An example of transformation of the coordinate system by the direction cosine matrix E is described more specifically. In a case where the base vector of the inertial coordinate system is $[x_i, y_i, z_i]$, and the base vector of the coordinate system with respect to the foot is $[x_b, y_b, z_b]$, a conversion formula between them is expressed by the following equation (1).

[Math. 1]

$$\begin{bmatrix} x_b \\ y_b \\ z_b \end{bmatrix} = \begin{bmatrix} E_{11} & E_{12} & E_{13} \\ E_{21} & E_{22} & E_{23} \\ E_{31} & E_{32} & E_{33} \end{bmatrix} \begin{bmatrix} x_i \\ y_i \\ z_i \end{bmatrix} = E \begin{bmatrix} x_i \\ y_i \\ z_i \end{bmatrix} \quad (1)$$

In a case where angle acquired by rotating the base vector of the inertial coordinate system by angles of ψ (psi), θ (theta), and φ (phi) in the order of z, y, and x is an Euler angle of the coordinate system transformation, the direction cosine matrix E is expressed by the following equation (2).

[Math. 2]

$$E = \begin{bmatrix} 1 & 0 & 0 \\ 0 & \cos\phi & \sin\phi \\ 0 & -\sin\phi & \cos\phi \end{bmatrix} \begin{bmatrix} \cos\theta & 0 & -\sin\theta \\ 0 & 1 & 0 \\ \sin\theta & 0 & \cos\theta \end{bmatrix} \begin{bmatrix} \cos\psi & \sin\psi & 0 \\ -\sin\psi & \cos\psi & 0 \\ 0 & 0 & 1 \end{bmatrix} =$$

$$\begin{bmatrix} \cos\theta\cos\psi & \cos\theta\sin\psi & -\sin\theta \\ \sin\phi\sin\theta\cos\psi - \cos\phi\sin\psi & \sin\phi\sin\theta\sin\psi + \cos\phi\cos\psi & \sin\phi\cos\theta \\ \cos\phi\sin\theta\cos\psi + \sin\phi\sin\psi & \cos\phi\sin\theta\sin\psi - \sin\phi\cos\psi & \cos\phi\cos\theta \end{bmatrix} \quad (2)$$

Note that the calculation method used for conversion of the coordinate system is merely an example, and other calculation methods may be used. For example, a calculation method using a quaternion may be applied.

In step S103, the angle calculation unit 132 calculates the angle between the sole of the user 4 and the ground from the angular velocity in the three axial directions and the acceleration in the three directions after being transformed into the coordinate system with respect to the foot of the user 4. As a specific example of this process, there is a method in which angular velocity in three axial directions and acceleration in three directions are input to a Madgwick filter (Non Patent Literature 1), and a rotation angle in three axial directions of the foot is output. The rotation angles in the three axial directions acquired by the Madgwick filter are the angles of adduction or abduction of the foot, the angle of pronation or supination of the foot, and the angle of bending or stretching of the foot. Of these three angles, the angle of stretching or bending of the foot corresponds to the angle between the sole of the foot of the user 4 and the ground.

In step S104, the determination unit 130 performs a pedaling state determination process for determining whether or not the user 4 is in a pedaling state in which the user 4 is pedaling the bicycle, based on at least the above-described angle.

Figure 6:
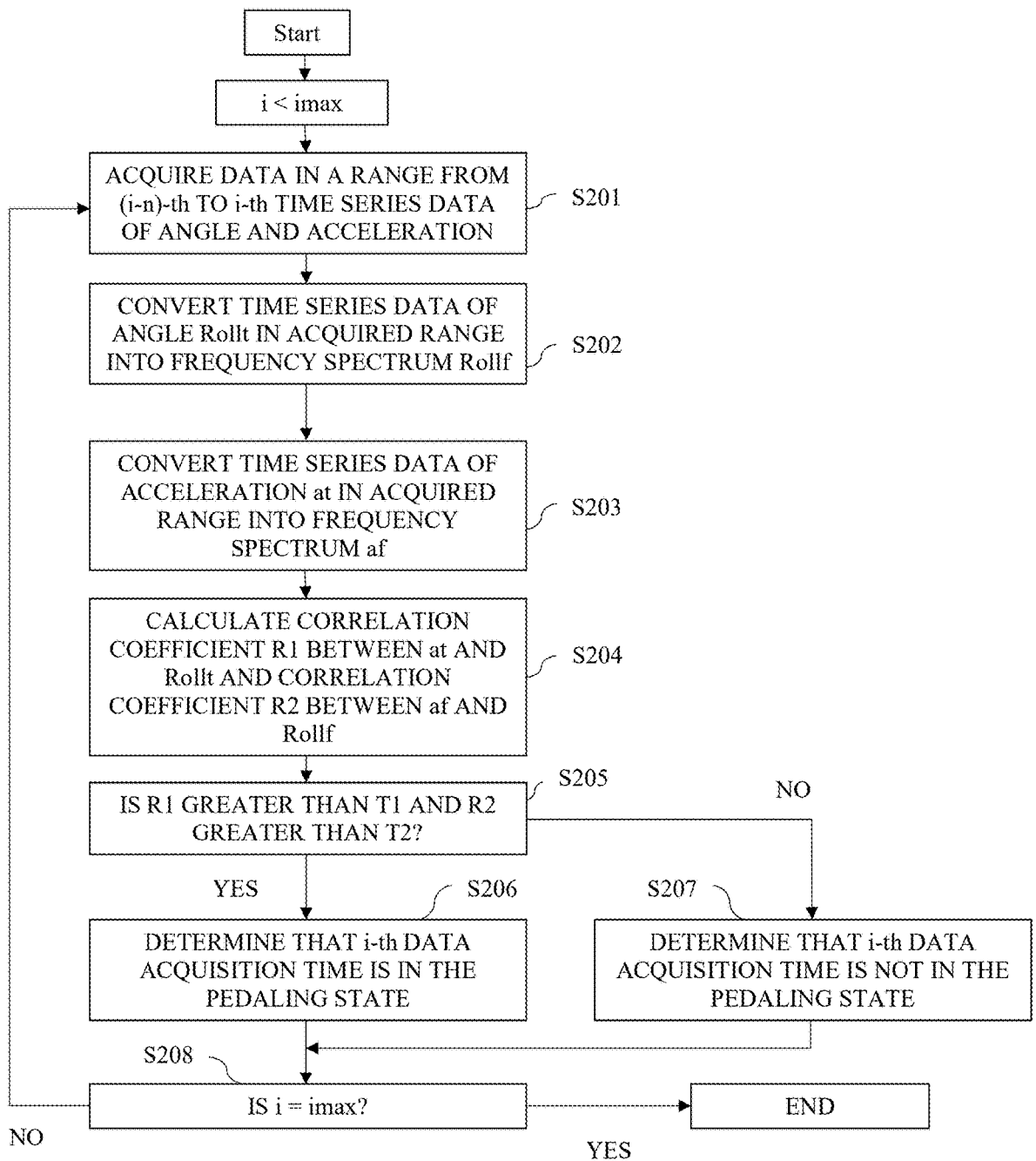
FIG. 6 is a flowchart illustrating an example of a pedaling state determination process.

FIG. 6 is a flowchart illustrating an example of a pedaling state determination process. The process of FIG. 6 is a subroutine corresponding to step S104 of FIG. 5. This process is a loop process in which steps S201 through S207 are repeated for each data. In FIG. 6, i represents a data number of time series data of the input angle and acceleration. The process from steps S201 through step S207 are repeated until the data number reaches the predetermined upper limit value imax from the initial value.

In step S201, the data selecting unit 133 acquires data in the range from the (i–n)-th to the i-th of the time series data of the angle and the time series data of the acceleration. This process is for specifying a time range of time series data used for conversion into a frequency domain in step S202 and step S203 described later. Therefore, the process of the data selecting unit 133 corresponds to a process of multiplying the time series data by a rectangular window having a width n. Note that the process may be modified to use another window function, and for example, a Gaussian window, a Hanning window, or the like may be applied.

In step S202, the data conversion unit 134 converts the time series data of the angle $Roll_t$ in the range acquired in step S201 into the frequency spectrum $Roll_f$. This process may be any process as long as it can convert time domain data into frequency domain data, and may be Fourier transform, for example. The algorithm used for the Fourier transform may be, for example, a fast Fourier transform.

In step S203, as in step S202, the data conversion unit 134 converts the time series data of the acceleration $a_t$ in the range acquired in step S201 into the frequency spectrum $a_f$.

In step S204, the similarity degree calculation unit 135 calculates a correlation coefficient R1 between time series data of the acceleration at and time series data of the angle $Roll_t$. Further, the similarity degree calculation unit 135 calculates a correlation coefficient R2 between the frequency spectrum of the acceleration $a_f$ and the frequency spectrum of the angle $Roll_f$. Note that the correlation coefficients R1 and R2 may typically be Pearson's product moment correlation coefficients. The correlation coefficients R1 and R2 may be referred to as a first similarity degree and a second similarity degree, respectively.

In step S205, the comparison unit 136 compares the correlation coefficients R1 and R2 with predetermined threshold values T1 and T2. When the correlation coefficient R1 is greater than the threshold value T1 and the correlation coefficient R2 is greater than the threshold value T2 (YES in step S205), the process proceeds to step S206. If the above condition is not satisfied (NO in step S205), the process proceeds to step S207. The threshold values T1 and T2 may be more generally referred to as a first threshold value and a second threshold value, respectively.

In step S206, the determination unit 130 determines that the user 4 pedaled the bicycle at the i-th data acquisition time (that is, the user 4 was in the pedaling state). The determination result is stored in the storage unit 140 in association with the data number i or the time corresponding thereto.

In step S207, the determination unit 130 determines that the user 4 did not pedal the bicycle at the i-th data acquisition time (that is, the user 4 was not in the pedaling state). The determination result is stored in the storage unit 140 in association with the data number i or the time corresponding thereto.

In step S208 the determination unit 130 determines whether data number of time series data of the input angle and acceleration i is equal to the predetermined upper limit value imax. When the determination is yes, the process ends. When the determination is no, the process is repeated in a loop from steps S201 through step S207 until the data number i reaches the predetermined upper limit value imax from the initial value.

Figure 7:
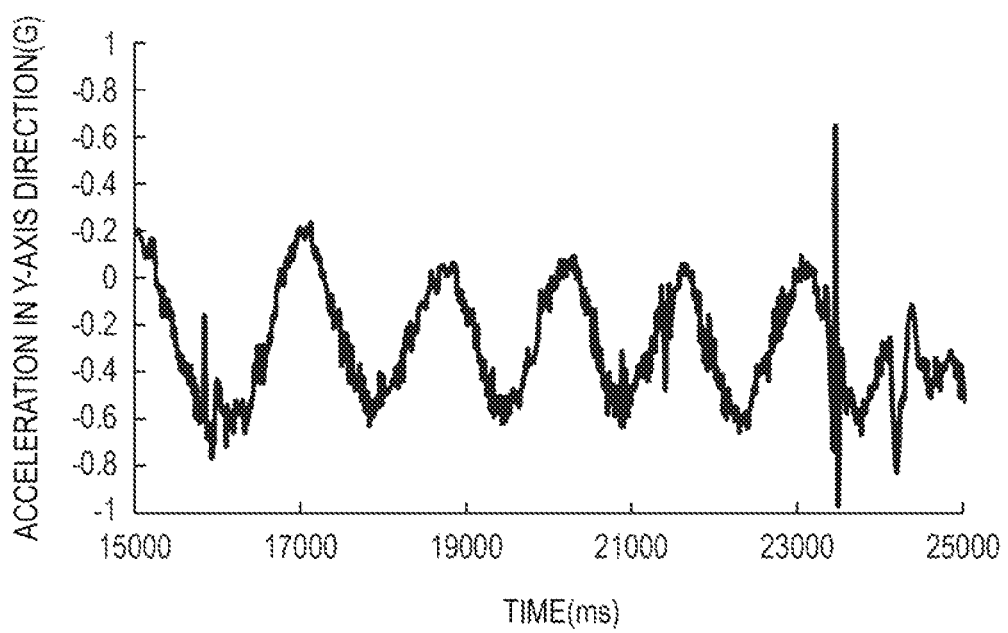
FIG. 7 is a graph illustrating an example of time series data of acceleration in a pedaling state.

In the above-described pedaling state determination process, the angle between the sole of the foot and the ground is used for determination. The reason why it is possible to accurately determine whether or not the user 4 is pedaling is described. FIG. 7 is a graph illustrating an example of time series data of acceleration in a pedaling state. The horizontal axis of FIG. 7 represents time in units of milliseconds (ms), and the vertical axis of FIG. 7 represents acceleration in the y-axis direction, that is, in the longitudinal direction of the foot. The unit G of the vertical axis is a unit of acceleration based on the standard gravitational acceleration (about 9.8 m/s$^2$). When the user 4 is pedaling, the foot of the user 4 is rotating, so that the acceleration has a waveform close to a sine wave. As can be understood from FIG. 7, the acceleration includes large noise due to various factors such as vibration of the bicycle. In some cases, as in the vicinity of 23500 ms in FIG. 7, a large noise exceeding the amplitude of the sine wave may be generated, and if the determination of the pedaling state is performed using only the acceleration, such noise may affect the determination accuracy.

Figure 8:
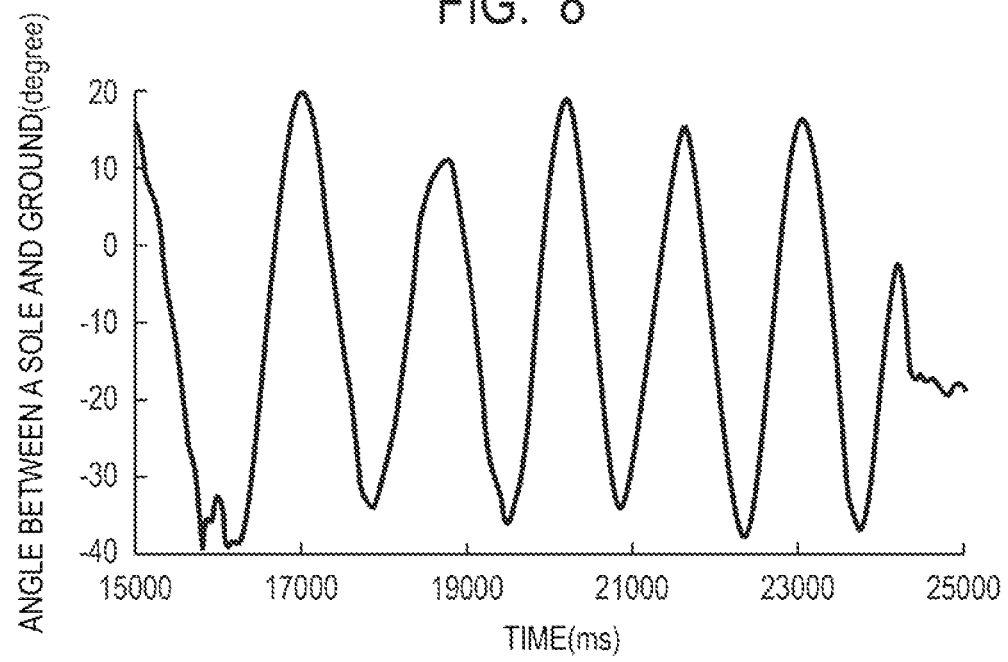
FIG. 8 is a graph illustrating an example of time series data of an angle between a sole and ground in the pedaling state.

FIG. 8 is a graph illustrating an example of time series data of an angle between a sole and ground in a pedaling state. The horizontal axis of FIG. 8 represents time, and the vertical axis of FIG. 8 represents the angle between the sole of the foot and the ground. As can be understood from FIG. 8, the noise included in the angle is smaller than the noise included in the acceleration. Therefore, determination accuracy can be improved by performing determination of the pedaling state using an algorithm utilizing the angle.

Figure 9:
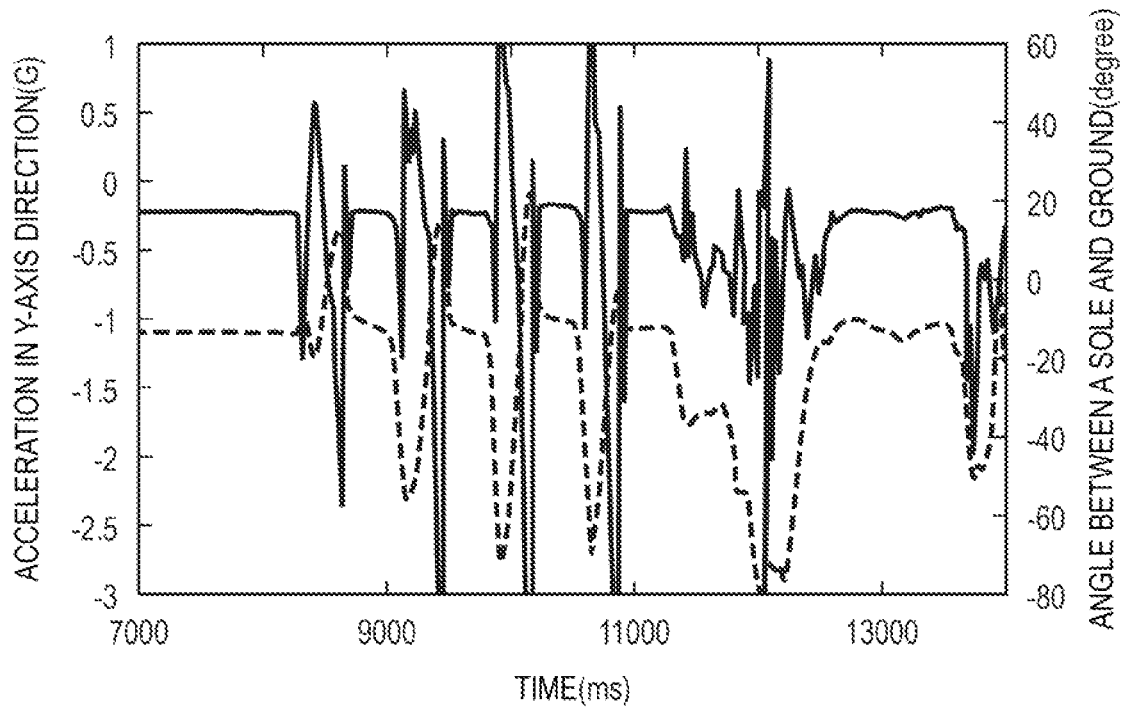
FIG. 9 is a graph illustrating an example of time series data of the acceleration and time series data of the angle when a user is walking.

In the above-described pedaling state determination process, the determination is performed using the correlation coefficient between the acceleration and the angle. The reason why whether or not the user 4 is pedaling can be determined with higher accuracy is described. First, waveforms of acceleration and angle when the user 4 is walking is described with reference to FIG. 9 and FIG. 10 as an example of a case where the user 4 is not pedaling (non-pedaling state). FIG. 9 is a graph illustrating an example of time series data of acceleration and time series data of angle when the user 4 is walking. The horizontal axis of FIG. 9 represents time, the left axis of FIG. 9 represents acceleration in the y-axis direction, and the right axis of FIG. 9 represents an angle between the sole of the foot and the ground. The solid line graph of FIG. 9 indicates the acceleration of the left axis, and the broken line graph of FIG. 9 indicates the angle of the right axis.

Figure 10:
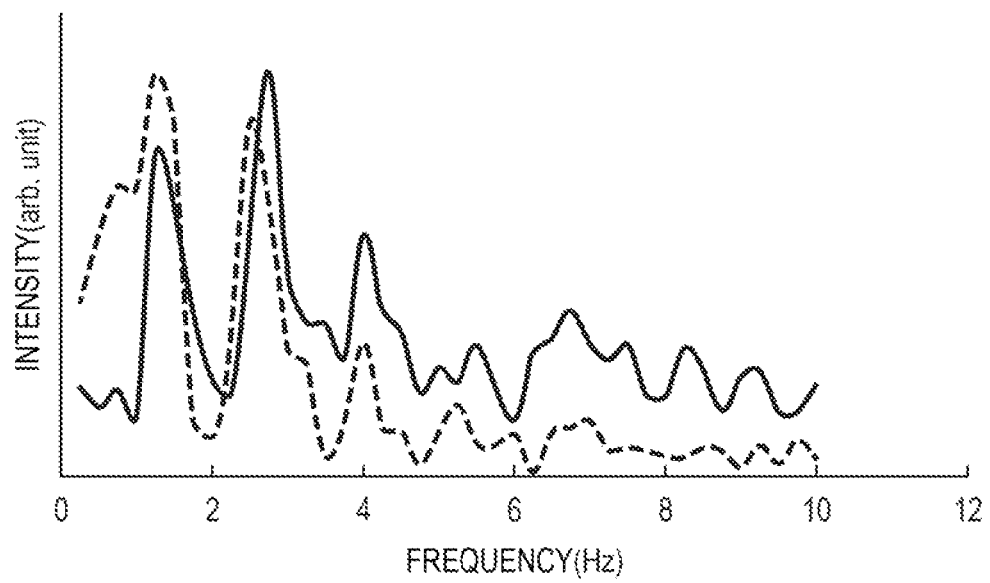
FIG. 10 is a graph illustrating an example of frequency spectrum of the acceleration and frequency spectrum of the angle when the user is walking.

FIG. 10 is a graph illustrating an example of a frequency spectrum of acceleration and a frequency spectrum of angle when the user 4 is walking. The horizontal axis of FIG. 10 represents the frequency in units of Hertz (Hz), and the vertical axis of FIG. 10 represents the intensity in arbitrary units. The solid line graph of FIG. 10 represents the frequency spectrum of the acceleration, and the broken line graph of FIG. 10 represents the frequency spectrum of the angle.

As can be understood from FIG. 9 and FIG. 10, when the user 4 walks, the waveform of the acceleration and the waveform of the angle are not similar to each other in both the time series data and the frequency spectrum. Therefore, when the user 4 walks, the correlation coefficient between the acceleration and the angle is a small value.

Figure 11:
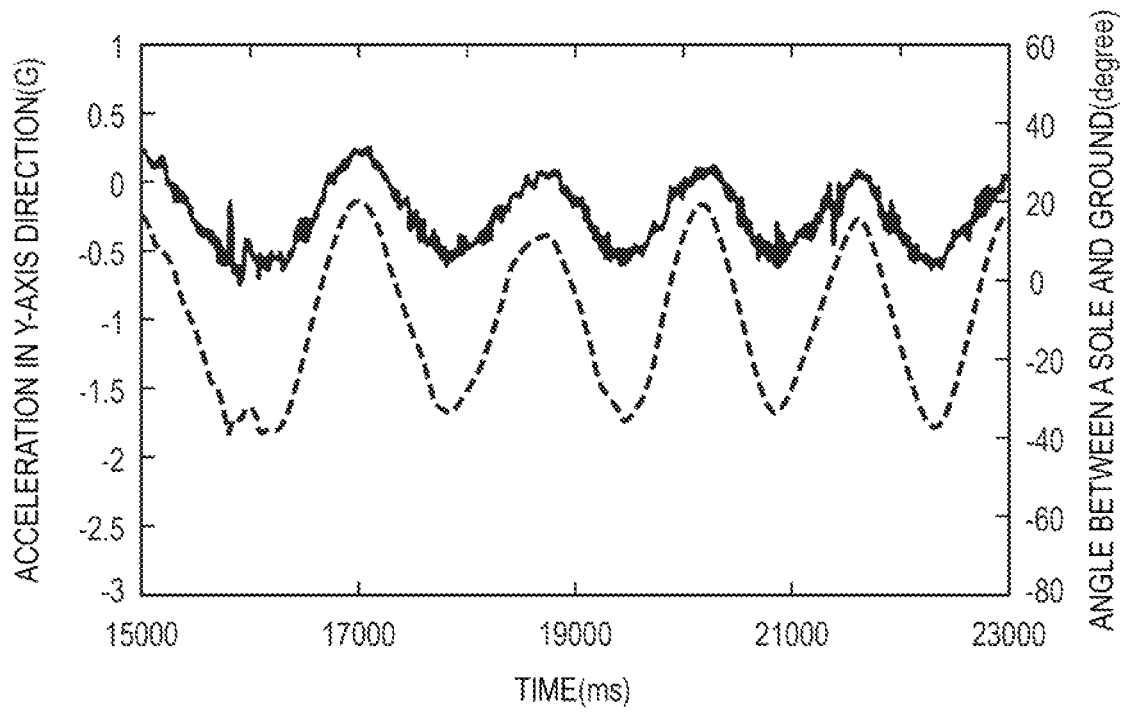
FIG. 11 is a graph illustrating an example of time series data of the acceleration and time series data of the angle in the pedaling state.
Figure 12:
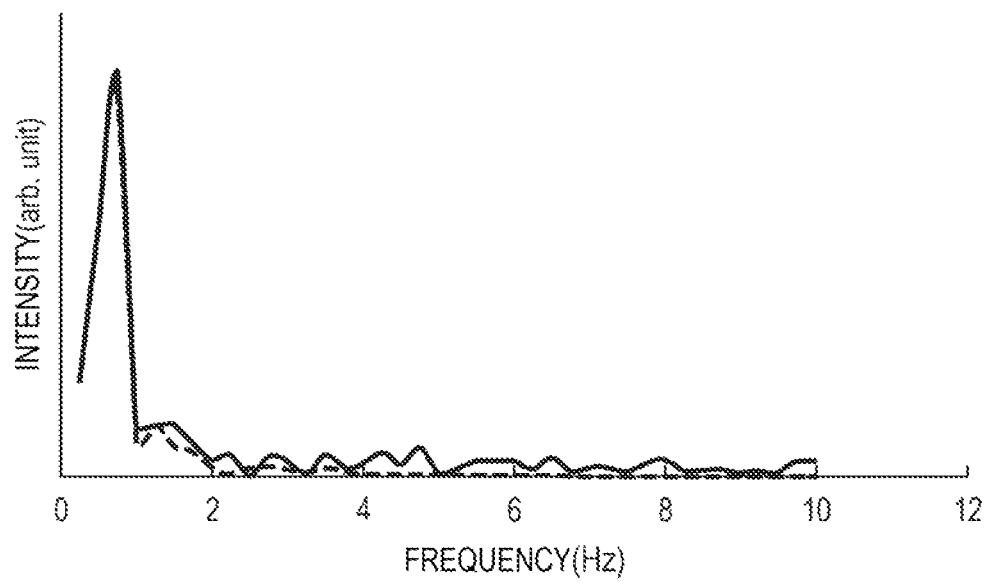
FIG. 12 is a graph illustrating an example of frequency spectrum of the acceleration and frequency spectrum of the angle in the pedaling state.

Next, waveforms of acceleration and angle when the user 4 is pedaling (pedaling state) is described with reference to FIG. 11 and FIG. 12. The notations of the graphs are the same as those in FIG. 9 and FIG. 10, and therefore the description thereof is omitted. As can be understood from FIG. 11 and FIG. 12, in both the time series data and the frequency spectrum, the waveform of the acceleration and the waveform of angle are similar to each other. Therefore, in the pedaling state, the correlation coefficient between the acceleration and the angle is greater than that in the walking state.

As described above, in the pedaling state, the similarity degree between the acceleration and the angle is high and the correlation coefficient is large as compared with the non-pedaling state. Therefore, the correlation coefficient is calculated as an index of the similarity degree between the acceleration and the angle, and the magnitude relation between the correlation coefficient and the threshold value is used as the determination condition, whereby it is possible to determine the pedaling state with higher accuracy. An index other than the correlation coefficient may be used as long as the determination method uses the similarity degree between the acceleration and the angle. For example, covariance may be used as a determination condition.

Further, in this determination, by referring to both the time series data, which is the waveform in the time domain, and the frequency spectrum, which is the waveform in the frequency domain, it is possible to more reliably determine the pedaling state. However, the determination may be performed using only the time series data or using only the frequency spectrum. In this case, the process is simplified, and the amount of calculation can be reduced.

As described above, according to the present example embodiment, the information processing device 11 is provided that can accurately determine the state of the user 4 riding the bicycle by determining whether or not the user 4 is in the pedaling state based on the angle between the sole of the foot and the ground.

SECOND EXAMPLE EMBODIMENT

The energy calculation system of the present example embodiment is an example of utilizing the function of determining the pedaling state by the state determination system of the first example embodiment. There is a need to acquire a log of daily energy consumption (so-called consumed calories). As a part of health management, the energy calculation system is a system that can meet the above needs by calculating the energy consumed by the user 4 when the user 4 rides the bicycle. Description of portions common to those in the first example embodiment is omitted.

Figure 13:
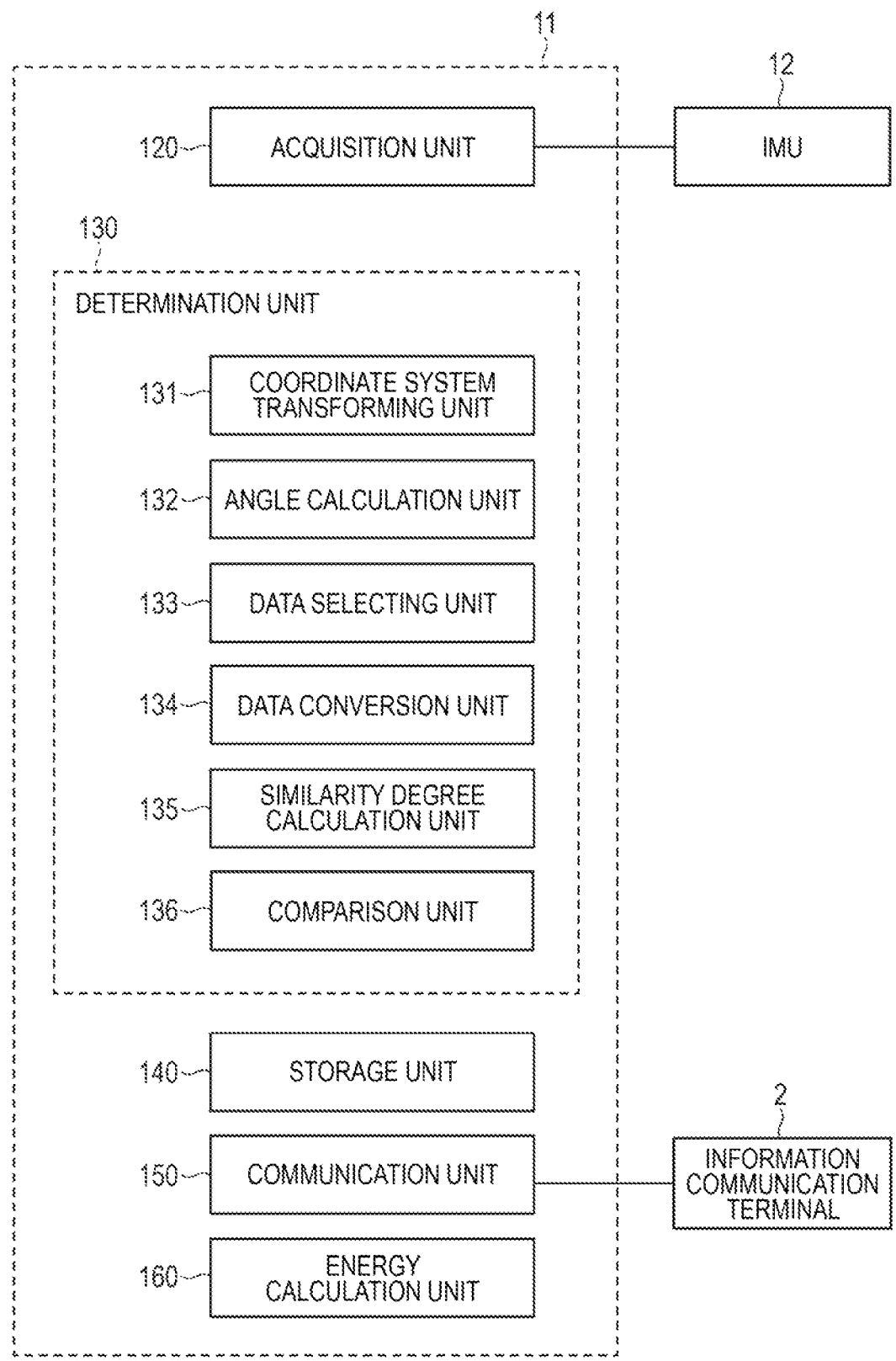
FIG. 13 is a functional block diagram of an information processing device according to a second example embodiment.

FIG. 13 is a functional block diagram of the information processing device 11 included in the energy calculation system according to the present example embodiment. The energy calculation system of the present example embodiment is acquired by adding an energy calculation unit 160 to the information processing device 11 of the state determination system of the first example embodiment. The CPU 111 realizes the function of the energy calculation unit 160 by loading a program stored in the ROM 113, the flash memory 114, or the like into the RAM 112 and executing the program. In FIG. 13, the energy calculation unit 160 is provided in the information processing device 11, but this function may be provided in the information communication terminal 2 or the server 3.

Figure 14:
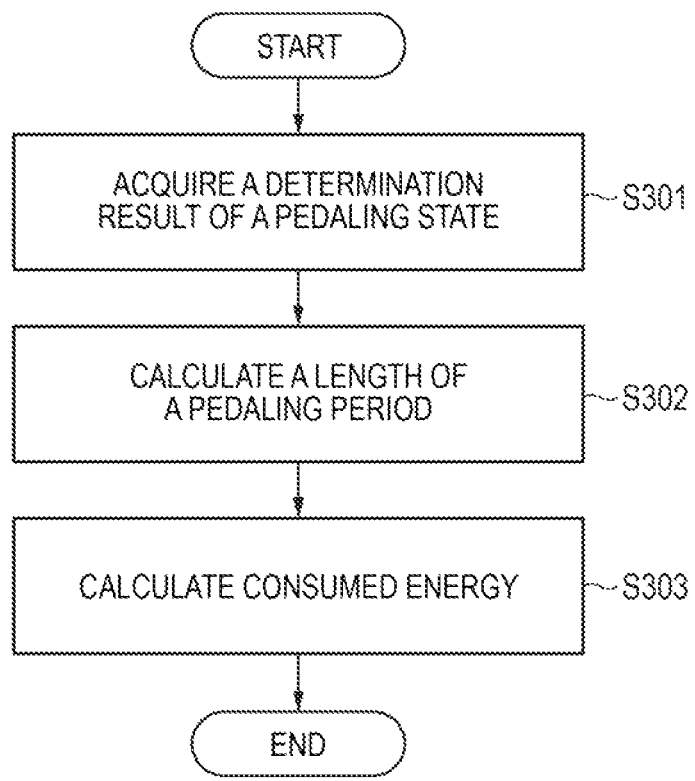
FIG. 14 is a flowchart illustrating an example of an energy calculation process performed by the energy calculation unit according to the second example embodiment.

FIG. 14 is a flowchart illustrating an example of an energy calculation process performed by the energy calculation unit 160 according to the present example embodiment. The process of FIG. 14 is performed, for example, after the end of the process according to the flowchart of FIG. 5. Alternatively, the process of FIG. 14 may be performed based on an operation of energy calculation by the user 4.

In step S301, the energy calculation unit 160 acquires the determination result of the pedaling state corresponding to each data acquisition time from the storage unit 140. In step S302, the energy calculation unit 160 adds up the period in the pedaling state (pedaling period) and calculates the length of the pedaling period in the data acquisition period.

In step S303, the energy calculation unit 160 calculates the energy consumed by the user 4 due to the riding of the bicycle by the user 4, based on the length of the pedaling period. For example, the following Equation (3) can be used as a calculation equation used for this calculation.

$$\text{Consumed energy} = \text{exercise intensity (METs)} \times \text{length of pedaling period} \times \text{body weight} \times \text{coefficient} \quad (3)$$

In Equation (3), METs, which is a unit of exercise intensity, represents how many times the energy consumption is as compared with the rest state during exercise. Depending on the speed, the inclination of the riding route, and the like, the METs of the bicycle riding is, for example, 4.0 (METs) or 6.8 (METs). The value of the exercise intensity may be input by the user 4 in advance with reference to a METs table or the like, or may be automatically set based on the speed of the bicycle or the like calculated from the acceleration acquired by the IMU 12. In Equation (3), the coefficient is about 1.05 when the unit of the length of the pedaling period is time (hour), the unit of the body weight is kg, and the unit of the consumed energy is kcal.

In the pedaling state, by pedaling, the energy consumption is increased as compared with the case of the non-pedaling state. By focusing attention on the length of the pedaling period, the energy calculation unit 160 of the present example embodiment can calculate the consumed energy more accurately than the case where the consumed energy is calculated based only on the length of time during which the user 4 is on the bicycle.

The energy calculation system of the present example embodiment uses the information processing device 11 that can accurately determine the state of the user 4 riding the bicycle. Thus, an energy calculation system capable of accurately calculating consumed energy is provided.

The device or system described in the above example embodiments can also be configured as in the following third example embodiment.

THIRD EXAMPLE EMBODIMENT

Figure 15:
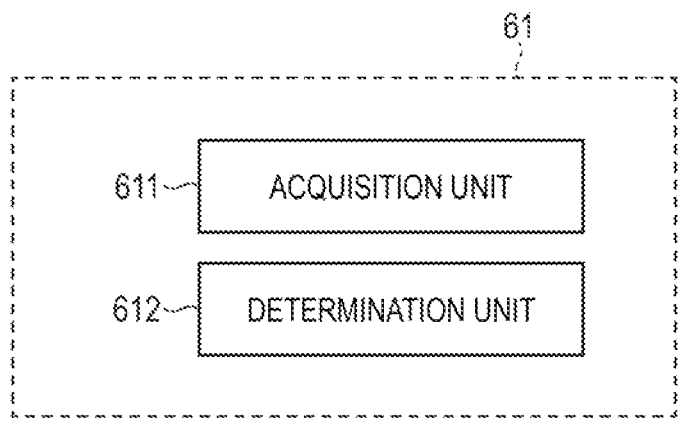
FIG. 15 is a functional block diagram of an information processing device according to a third example embodiment.

FIG. 15 is a functional block diagram of the information processing device 61 according to the third example embodiment. The information processing device 61 includes an acquisition unit 611 and a determination unit 612. The acquisition unit 611 acquires motion information of a foot of a user measured by a motion measurement device. The determination unit 612 determines whether or not the user is in a pedaling state in which the user pedals a bicycle based on an angle between a sole and a ground generated from the motion information.

According to the present example embodiment, the information processing device 61 capable of accurately determining the state of the user riding the bicycle is provided.

Modified Example Embodiments

The present invention is not limited to the example embodiments described above, and may be suitably modified within the scope of the present invention. For example, an example in which a part of the configuration of one example embodiment is added to another example embodiment or an example in which a part of the configuration of one example embodiment is replaced with another example embodiment is also an example embodiment of the present invention.

In the above-described example embodiments, the motion measurement device including the angular velocity sensor that measures the angular velocity in the three axial directions and the acceleration sensor that measures the acceleration in the three directions is used, but sensors other than these may also be used. For example, a magnetic sensor that detects geomagnetism by detecting magnetism in three directions to identify an azimuth may be further used. Even in this case, the same processing as the above-described example embodiments can be applied, and the accuracy can be further improved. Further, a global positioning system (GPS) receiver may also be used. In this case, the current position of the bicycle can be acquired, and the log of the position information and the speed information can be acquired.

Although the state determination process is performed inside the state determination device 1 in the above-described example embodiment, this function may be provided in the information communication terminal 2. In this case, the information communication terminal 2 functions as a state determination device.

A processing method in which a program for operating the configuration of the above-described example embodiments are recorded in a storage medium so as to implement the functions of the above-described example embodiment, the program recorded in the storage medium is read as code, and the program is executed in a computer is also included in the scope of each example embodiment. That is, a computer-readable storage medium is also included in the scope of the example embodiments. Further, not only the storage medium in which the above program is recorded, but also the program itself is included in each example embodiment. In addition, one or more components included in the above-described example embodiments may be a circuit such as an application specific integrated circuit (ASIC), a field programmable gate array (FPGA) configured to implement the functions of each component.

As the storage medium, for example, a floppy (registered trademark) disk, a hard disk, an optical disk, a magneto-optical disk, a compact disk (CD)-ROM, a magnetic tape, a nonvolatile memory card, or a ROM can be used. Further, the scope of each example embodiment is not limited to the case where the processing is executed by the program alone recorded in the storage medium, and a case where the processing is executed by operating on an operating system (OS) in cooperation with the functions of other software and extension board is also included in the scope of each example embodiment.

The service realized by the functions of the above-described example embodiments may be provided to the user in the form of a software as a service (SaaS).

It should be noted that the above-described example embodiments are merely examples of embodying the present invention, and the technical scope of the present invention should not be limitedly interpreted by these. That is, the present invention can be implemented in various forms without departing from the technical idea or the main features thereof.

The whole or part of the example embodiments disclosed above can be described as, but not limited to, the following supplementary notes.

(Supplementary Note 1)

An information processing device comprising:
 an acquisition unit configured to acquire motion information of a foot of a user measured by a motion measurement device; and
 a determination unit configured to determine whether or not the user is in a pedaling state in which the user pedals a bicycle based on an angle between a sole and a ground generated from the motion information.

(Supplementary Note 2)

The information processing device according to supplementary note 1, wherein the motion information includes acceleration of the foot.

(Supplementary Note 3)

The information processing device according to supplementary note 2, wherein the determination unit determines whether or not the user is in the pedaling state further based on the acceleration.

(Supplementary Note 4)

The information processing device according to supplementary note 3, wherein the determination unit determines whether or not the user is in the pedaling state based on time series data of the angle and time series data of the acceleration.

(Supplementary Note 5)

The information processing device according to supplementary note 4, wherein the determination unit determines whether or not the user is in the pedaling state based on a first similarity degree between the time series data of the angle and the time series data of the acceleration.

(Supplementary Note 6)

The information processing device according to supplementary note 5, wherein the first similarity degree includes a correlation coefficient between the time series data of the angle and the time series data of the acceleration.

(Supplementary Note 7)

The information processing device according to any one of supplementary notes 4 to 6, wherein the determination unit determines whether or not the user is in the pedaling state further based on a frequency spectrum of the angle and a frequency spectrum of the acceleration acquired by transforming the time series data of the angle and the time series data of the acceleration into a frequency domain.

(Supplementary Note 8)

The information processing device according to supplementary note 7, wherein the determination unit determines whether or not the user is in the pedaling state based on a second similarity degree between the frequency spectrum of the angle and the frequency spectrum of the acceleration.

(Supplementary Note 9)

The information processing device according to supplementary note 8, wherein the second similarity degree includes a correlation coefficient between the frequency spectrum of the angle and the frequency spectrum of the acceleration.

(Supplementary Note 10)

The information processing device according to supplementary note 8 or 9, wherein the determination unit determines the user is in the pedaling state in a case where a first similarity degree between the time series data of the angle and the time series data of the acceleration is greater than a first threshold value and a second similarity degree between the frequency spectrum of the angle and the frequency spectrum of the acceleration is greater than a second threshold value.

(Supplementary Note 11)

The information processing device according to any one of supplementary notes 4 to 10, wherein the time series data includes at least two pedaling cycles.

(Supplementary Note 12)

The information processing device according to any one of supplementary notes 2 to 11, wherein the motion information further includes angular velocity of the foot.

(Supplementary Note 13)

The information processing device according to supplementary note 12, wherein the determination unit transforms a coordinate system of the acceleration and the angular velocity included in the motion information into a coordinate system with respect to the foot.

(Supplementary Note 14)

The information processing device according to supplementary note 12 or 13, wherein the determination unit calculates the angle using the acceleration and the angular velocity.

(Supplementary Note 15)

The information processing device according to supplementary note 14, wherein the determination unit calculates the angle using a Madgwick filter.

(Supplementary Note 16)

The information processing device according to any one of supplementary notes 1 to 15, wherein the motion measurement device is provided at a position corresponding to an arch of the foot.

(Supplementary Note 17)

A state determination system comprising:
the information processing device according to any one of supplementary notes 1 to 16; and
the motion measurement device.

(Supplementary Note 18)

An energy calculation system comprising an energy calculation unit configured to calculate energy consumed by the user by riding the bicycle based on a time of the pedaling state acquired by the information processing device according to any one of supplementary notes 1 to 16.

(Supplementary Note 19)

An information processing method comprising:
acquiring motion information of a foot of a user measured by a motion measurement device; and
determining whether or not the user is in a pedaling state in which the user pedals a bicycle based on an angle between a sole and a ground generated from the motion information.

(Supplementary Note 20)

A storage medium storing a program that causes a computer to perform:
acquiring motion information of a foot of a user measured by a motion measurement device; and
determining whether or not the user is in a pedaling state in which the user pedals a bicycle based on an angle between a sole and a ground generated from the motion information.

REFERENCE SIGNS LIST 1 state determination device
2 information communication terminal
3 server
4 user
5 shoe
11, 61 information processing device
12 IMU
13 battery
111, 201 CPU
112, 202 RAM
113, 203 ROM
114, 204 flash memory
115, 205 communication I/F
116 IMU control device
120, 611 acquisition unit
130, 612 determination unit
131 coordinate system transforming unit
132 angle calculation unit
133 data selecting unit
134 data conversion unit
135 similarity degree calculation unit
136 comparison unit
140 storage unit
150 communication unit
160 energy calculation unit
206 input device
207 output device

What is claimed is:

1. An information processing device comprising:
a memory configured to store instructions; and
a processor configured to execute the instructions to:
acquire motion information of a foot of a user measured by a motion measurement device; and
determine whether or not the user is in a pedaling state in which the user pedals a bicycle based on an angle between a sole and a ground generated from the motion information.

2. The information processing device according to claim 1, wherein the motion information includes acceleration of the foot.

3. The information processing device according to claim 2, wherein whether or not the user is in the pedaling state is determined further based on the acceleration.

4. The information processing device according to claim 3, wherein whether or not the user is in the pedaling state is determined based on time series data of the angle and time series data of the acceleration.

5. The information processing device according to claim 4, wherein whether or not the user is in the pedaling state is determined based on a first similarity degree between the time series data of the angle and the time series data of the acceleration.

6. The information processing device according to claim 5, wherein the first similarity degree includes a correlation coefficient between the time series data of the angle and the time series data of the acceleration.

7. The information processing device according to claim 4, wherein whether or not the user is in the pedaling state is determined further based on a frequency spectrum of the angle and a frequency spectrum of the acceleration acquired by transforming the time series data of the angle and the time series data of the acceleration into a frequency domain.

8. The information processing device according to claim 7, wherein whether or not the user is in the pedaling state is determined based on a second similarity degree between the frequency spectrum of the angle and the frequency spectrum of the acceleration.

9. The information processing device according to claim 8, wherein the second similarity degree includes a correlation coefficient between the frequency spectrum of the angle and the frequency spectrum of the acceleration.

10. The information processing device according to claim 8, wherein the user is determined to be in the pedaling state in a case where a first similarity degree between the time series data of the angle and the time series data of the acceleration is greater than a first threshold value and a second similarity degree between the frequency spectrum of the angle and the frequency spectrum of the acceleration is greater than a second threshold value.

11. The information processing device according to claim 4, wherein the time series data includes at least two pedaling cycles.

12. The information processing device according to claim 2, wherein the motion information further includes angular velocity of the foot.

13. The information processing device according to claim 12, wherein a coordinate system of the acceleration and the angular velocity included in the motion information is transformed into a coordinate system with respect to the foot.

14. The information processing device according to claim 12, wherein the angle is calculated using the acceleration and the angular velocity.

15. The information processing device according to claim 14, wherein the angle is calculated using a Madgwick filter.

16. The information processing device according to claim 1, wherein the motion measurement device is provided at a position corresponding to an arch of the foot.

17. A state determination system comprising:
the information processing device according to claim 1; and
the motion measurement device.

18. An energy calculation system comprising:
a memory configured to store instructions; and
a processor configured to execute the instructions to calculate energy consumed by the user by riding the bicycle based on a time of the pedaling state acquired by the information processing device according to claim 1.

19. An information processing method comprising:
acquiring motion information of a foot of a user measured by a motion measurement device; and
determining whether or not the user is in a pedaling state in which the user pedals a bicycle based on an angle between a sole and a ground generated from the motion information.

20. A non-transitory storage medium storing a program that causes a computer to perform:
acquiring motion information of a foot of a user measured by a motion measurement device; and
determining whether or not the user is in a pedaling state in which the user pedals a bicycle based on an angle between a sole and a ground generated from the motion information.

* * * * *